United States Patent [19]

Bennett, deceased

[11] Patent Number: Plant 7,188

[45] Date of Patent: Mar. 13, 1990

[54] MINIATURE ROSE PLANT NAMED 'HOT LIPS'

[76] Inventors: Cecilia L. D. Bennett, deceased, late of Chula Vista, Calif.; by Susan M. O'Brien, administrator, 489 Minot Ave., Chula Vista, Calif. 92010

[21] Appl. No.: 293,173

[22] Filed: Jan. 3, 1989

[51] Int. Cl.[4] ..... A01H 5/00

[52] U.S. Cl. ..... Plt./7

[58] Field of Search ..... Plt./7

*Primary Examiner*—James R. Feyrer

[57] ABSTRACT

The subject of the present disclosure is a new and distinct variety of miniature rose plant, named 'Hot Lips', which is characterized by its rich coral blooms, ranging from near Shrimp Red to near Chinese Coral to near Azalea Pink. The blooms are usually borne one to a stem with hybrid tea form but on occasion may be produced in sprays of 3 to 5 or more. The bush is vigorous, well-branched and produces moderate to heavy quantity of blooms.

1 Drawing Sheet

The present invention relates to a new and distinct variety of a hardy, dwarf, bush plant of the miniature class; the variety being primarily characterized as orange blend.

The variety is further characterized by:

Long stemmed blooms of hybrid tea-type form, borne usually one to a stem but on occasion in sprays of 3 to 5 or more. The blooms are held very erect and well above the foliage.

It has a slight fruity fragrance.

The plant ranges in height from 24 to 36 inches (60 to 90 cm). The canes are sturdy and erect with moderate branching and medium to heavy foilage covering. The plant is a moderate to heavy bloomer that does well either in the greenhouse or outdoors.

The plant has good growth habits, well-shaped and attractive, bearing numerous leaflets of average size. I have found this variety to be easily asexually reproduced from cuttings.

The seed parent was Futura (U.S. Plant Pat. No. 3,569), and the pollen parent was Why Not (miniature rose plant, red blend; R. S. Moore; introduced by Sequoia Nurseries, 1983). It differs from its seed parent in the following ways. It is a miniature rose in shades of coral, and Futura is a hybrid tea rose of orange-red. It differs from its pollen parent in the following ways. It has 25 to 30 petals of rich coral with hybrid tea form, and Why Not has fewer than 15 petals in a blending of red and yellow.

BRIEF DESCRIPTION OF THE DRAWING

The single color photographic view shows, in plan view, a bouquet of flowers of 'Hot Lips' in various stages of maturity from early bud stage to nearly full blown stage.

BOTANICAL DESCRIPTION

The descriptive matter which follows pertains to roses grown and color values observed in plants and newly opened blooms in the months of March through November 1988. The plants were grown outdoors in Chula Vista, Calif., and are believed to be accurate standards for this cultivar in similar conditions of soil and climate elsewhere.

Referring now specifically to the new and distinct variety of miniature rose plant named 'Hot Lips', the following is a detailed description thereof in outline; all major color plate identifications being by reference to The British Colour Council Horticultural Colour Chart, except where common terms of color definition are employed.

Type: Hardy, dwarf, bushy, greenhouse or outdoor, exhibition or garden decorative potted plant.

Class: Miniature.

Variety name: Hot Lips.

Flowers borne: Usually one to a stem, but occasionally in sprays of 3 to 5 or more on erect stems with foliage well below the blooms.

Quantity of bloom: Moderate to heavy both outdoors or greenhouse grown.

Bud:

*Peduncle.*—Average length (20 to 40 mm); average diameter and sturdy; ranging from near Scheeles Green (860/3 to 860 page 175) to near Lettuce Green (861/3 to 861 page 176) with occasional tinting of bronze.

*Hairs.*—Extremely small and reddish in color; located over the entire surface of the peduncle but none on the calyx.

*Calyx.*—Same color range as the peduncle.

*Opening.*—Opens well in all weather.

Bloom: *Size when fully open.*—Average for a miniature variety (50 to 60 mm).

*Petalage.*—Double—25 to 30 petals, arranged regularly, plus 3 to 5 petaloids.

*Form.*—Urn-shaped to ovoid as the bloom progresses. The petals remain somewhat cupped with the apex and/or margins reflexed outward, becoming at maturity more loosely cupped; and the petals reflex more tightly (quilling), until each row of petals forms a five-pointed star.

Petals: Fairly thick with good substance; both the upper and under surfaces of all petals have a matte finish.

*Shape.*—Outer petals are of a broad obovate form. The intermediate petals are very much like the outer petals only narrower. The inner petals are a broad lanceolate form; and the petaloids are also lanceolate with some occasional irregularities.

Color: Newly opened flowers from plants grown outdoors (March through November of 1988), Chula Vista, Calif.

*All petals.*—Upper and under surfaces—Ranging from near Shrimp Red (616/2 to 616 page 73) to near Chinese Coral (614/2 to 618 page 74) and to near Azales Pink (618/2 to 618 page 74) during warmer weather.

*General color effect.*—Newly opened flowers—Rich coral throughout. Three days open — Little or no fading of color. Three to five days open — Some slight fading of color, especially during warmer weather.

*Flower longevity.*—(March through November 1988) Plant in pot 3 to 5 days from bud with sepals reflexed to fully opened bloom. Holding at fully opened with only slight fading of color during warmer weather for 3 to 5 days longer. Cut bloom at livingroom temperature 5 to 7 days or longer.

Reproductive organs:

*Stamens.*—A generous amount arranged uniformly around the pistil.

*Filaments.*—Varying in length with shorter filaments more proximal to the pistil; golden yellow including the anthers.

*Pollen.*—Abundant.

*Pistil.*—Short, compact and abundant; reddish in color with pale yellow caps.

*Ovaries.*—All encased in calyx.

*Hips.*—Some.

*Seeds.*—3 to 5 or more in each hip.

*Sepals.*—Permanent; spear shaped; open as the bloom opens, recurving against the peduncle, when the bloom is fully opened.

Foliage:

*Leaves.*—Five to seven leaflets on the average; medium size for a miniature rose plant.

*Leaflets.*—Broad ovate-shaped.

*Margins.*—Very serrated with tinting of bronze, especially noticeable on the newer foliage.

*Color.*—Ranging from near Scheeles Green (860/2 to 860 page 175) to near Spinach Green (0960/2 to 0960/1 page 0960) with occasional bronzing of the margins, especially on the newer foliage. Upper surfaces have a semi-glossy finish, and the under surfaces have a matte finish of a slightly lighter shade than the upper surfaces.

*Rachis.*—Medium strength; upper surface is grooved with very small hairs over the length of it. Under surface has few if any hairs but does contain 2 to 5 small thorns.

*Stipules.*—Varying in length from small to medium; average width; tapering auricles angled outward at about 45 degrees.

Growth:

*Habit.*—Dwarf, bushy; average to tall in height for a miniature rose plant.

*Growth.*—Vigorous and well-branched.

*Canes.*—Medium diameter; sturdy; held erect.

*Main stems.*—Color range same as foliage.

*Thorns.*—Averaging 10 to 15 per 10 cm on the main stems and fewer on the branches. Reddish, straight and slender.

*Branches.*—Color range same as foliage.

The miniature rose plant and its flowers as herein described may vary in slight detail due to climate, soil and cultural conditions under which the variety may be grown; the present description being of the variety as grown in Chula Vista, Calif.

The following is claimed:

1. A new and distinct variety of miniature rose plant named, 'Hot Lips' of hardy, dwarf, vigorous growth, well-branched and attractive in appearance, substantially as illustrated and described, characterized by its hybrid tea-form blooms, ranging from near Shrimp Red to near Chinese Coral to near Azalea Pink, with flowers borne usually one to a stem but occasionally in sprays of 3 to 5 or more.

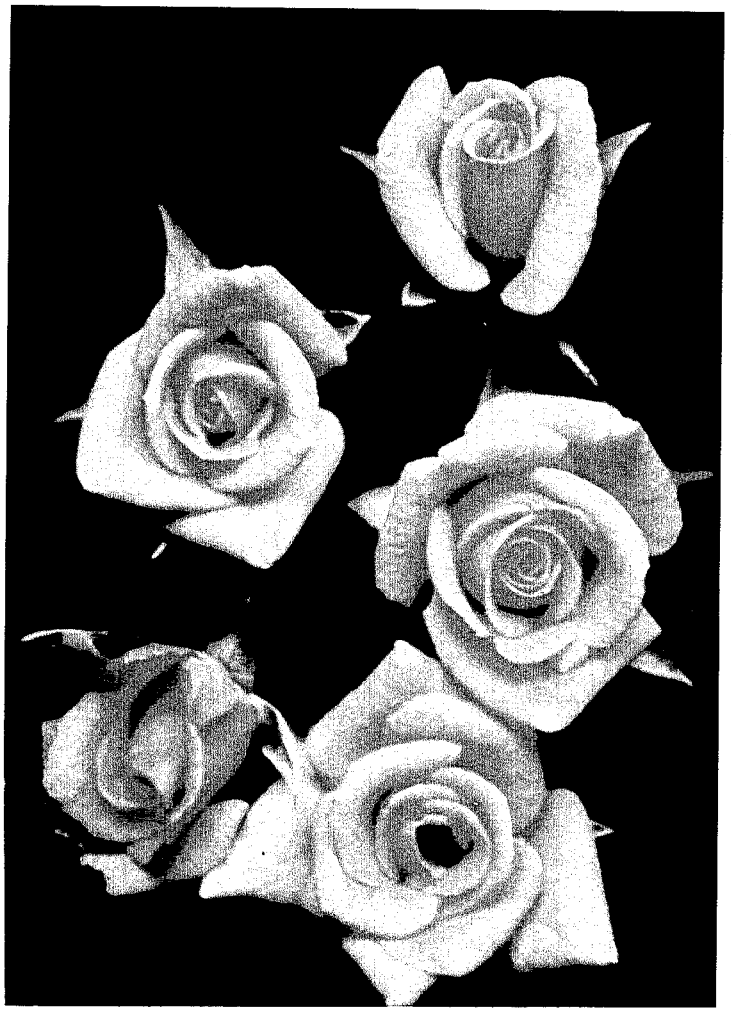

* * * * *